(12) United States Patent
Nagorny et al.

(10) Patent No.: US 8,261,741 B2
(45) Date of Patent: Sep. 11, 2012

(54) METHOD AND APPARATUS FOR BACKSPILL PREVENTION

(75) Inventors: Aleksandr Nagorny, Canoga Park, CA (US); David Sears, Woodland Hills, CA (US)

(73) Assignee: Resmed Limited, Bella Vista (AU)

( * ) Notice: Subject to any disclaimer, the term of this patent is extended or adjusted under 35 U.S.C. 154(b) by 1014 days.

(21) Appl. No.: 12/285,342

(22) Filed: Oct. 2, 2008

(65) Prior Publication Data

US 2009/0114221 A1    May 7, 2009

Related U.S. Application Data

(60) Provisional application No. 60/996,159, filed on Nov. 5, 2007.

(51) Int. Cl.
*A61M 11/00* (2006.01)

(52) U.S. Cl. .............................. 128/204.19; 128/204.18
(58) Field of Classification Search ............. 128/204.18, 128/204.19; 251/129.15, 129.21, 129.22
See application file for complete search history.

(56) References Cited

U.S. PATENT DOCUMENTS

| | | | | |
|---|---|---|---|---|
| 4,538,129 | A * | 8/1985 | Fisher | 335/230 |
| 6,000,417 | A * | 12/1999 | Jacobs | 137/2 |
| 6,068,010 | A * | 5/2000 | Reinicke | 137/1 |
| 6,253,789 | B1 * | 7/2001 | Krimmer et al. | 137/550 |
| 6,530,558 | B1 * | 3/2003 | Schulz | 251/129.21 |

* cited by examiner

*Primary Examiner* — Steven Douglas
(74) *Attorney, Agent, or Firm* — Nixon & Vanderhye P.C.

(57) ABSTRACT

A backspill prevention apparatus prevents water from a humidifier portion of a positive airway pressure (PAP) device from reaching a blower motor of a PAP device. The backspill prevention apparatus can include a variety of different devices, and is placed somewhere along an air passageway between a blower motor and a humidifier portion of a PAP device.

8 Claims, 15 Drawing Sheets

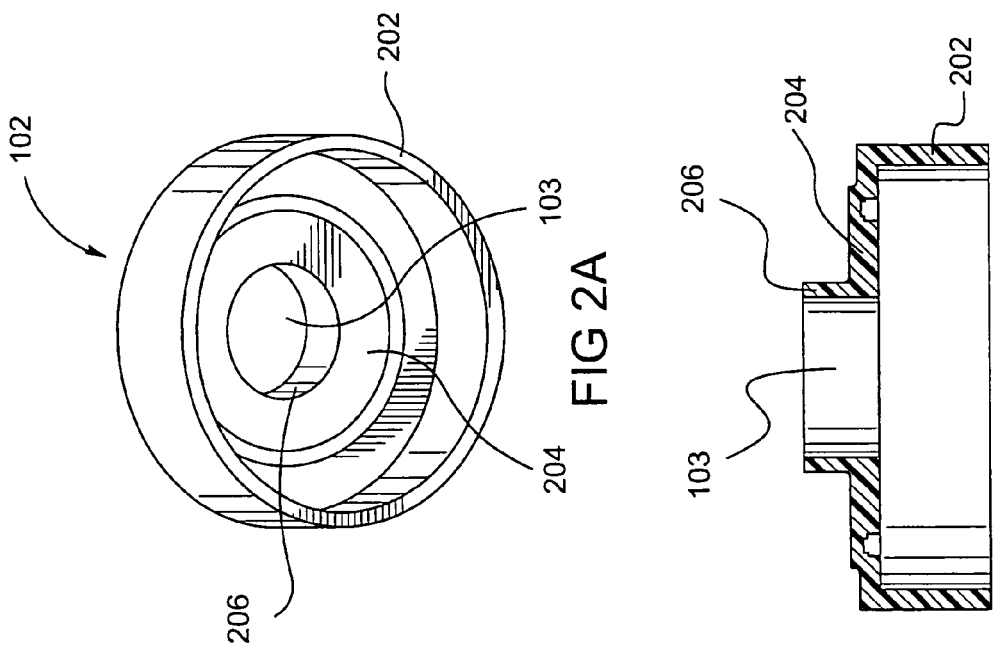
FIG 2A
FIG. 2B
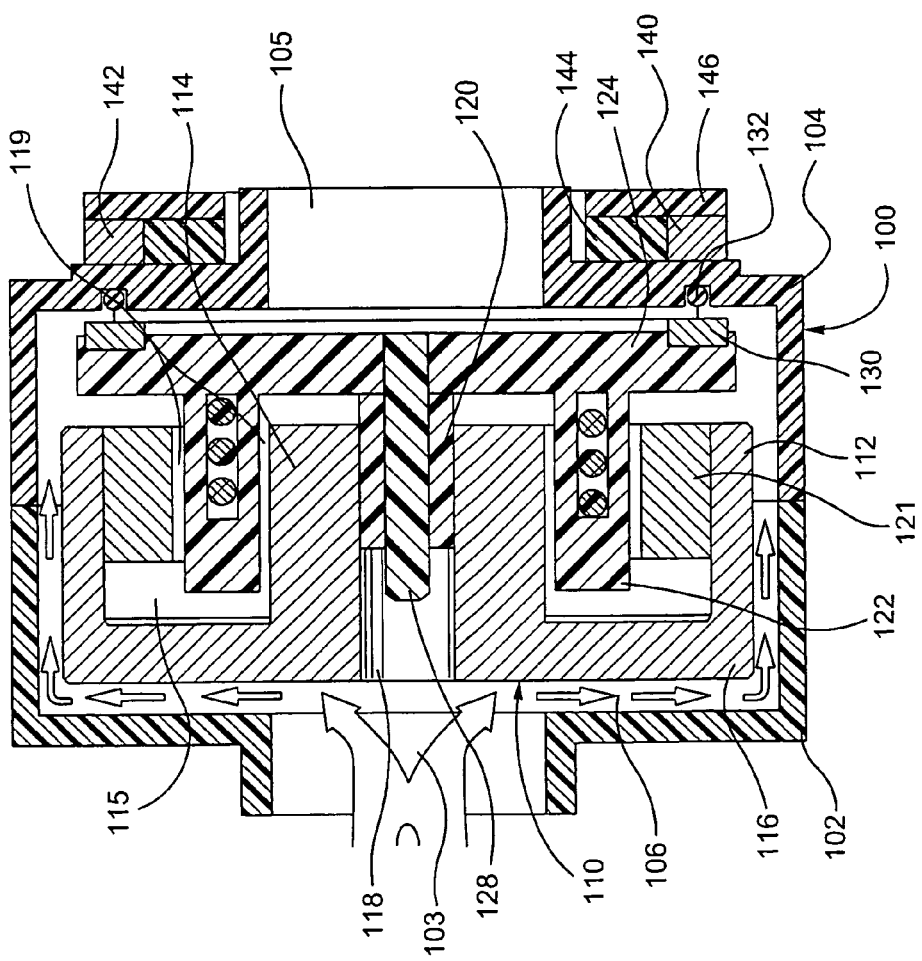
FIG. 1D

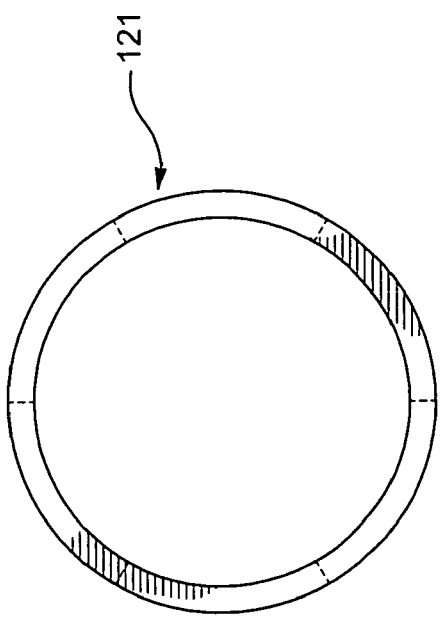
FIG. 4B
FIG. 4C
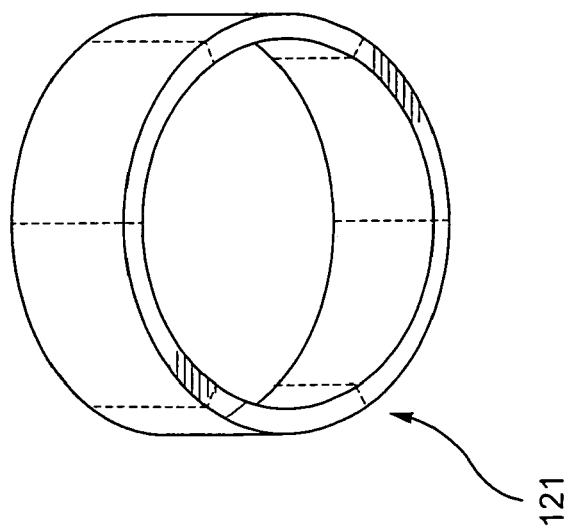
FIG. 4A

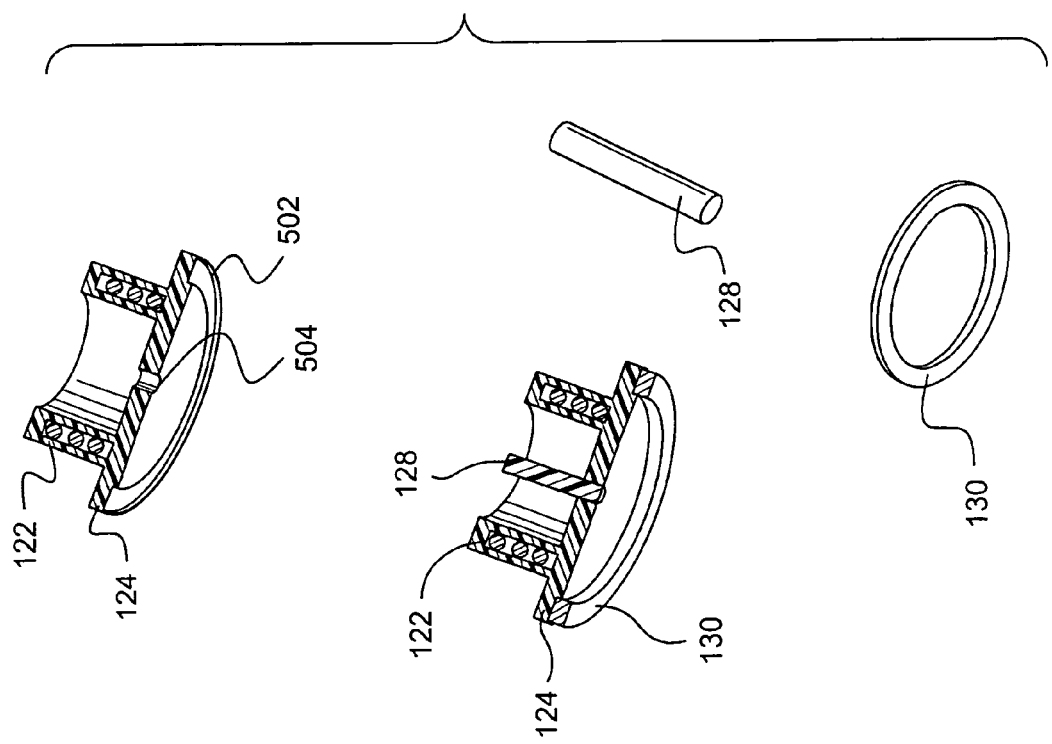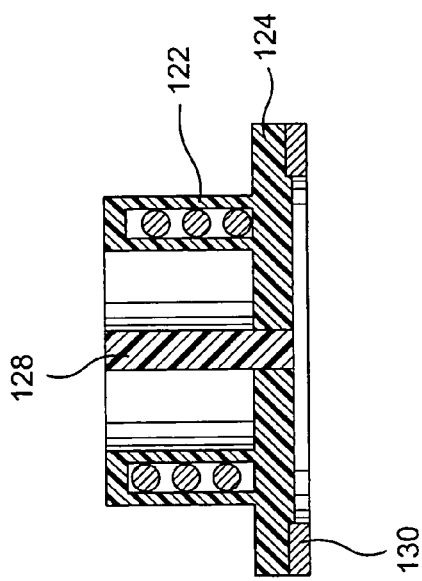

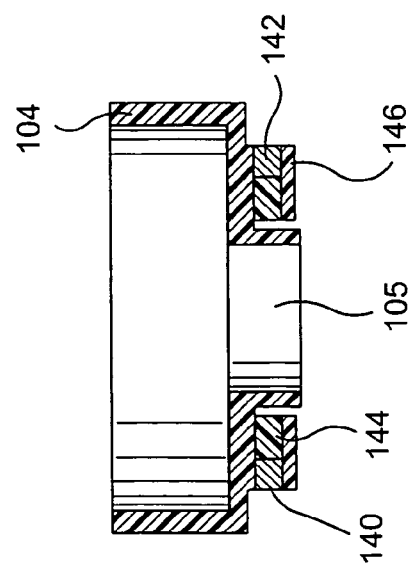
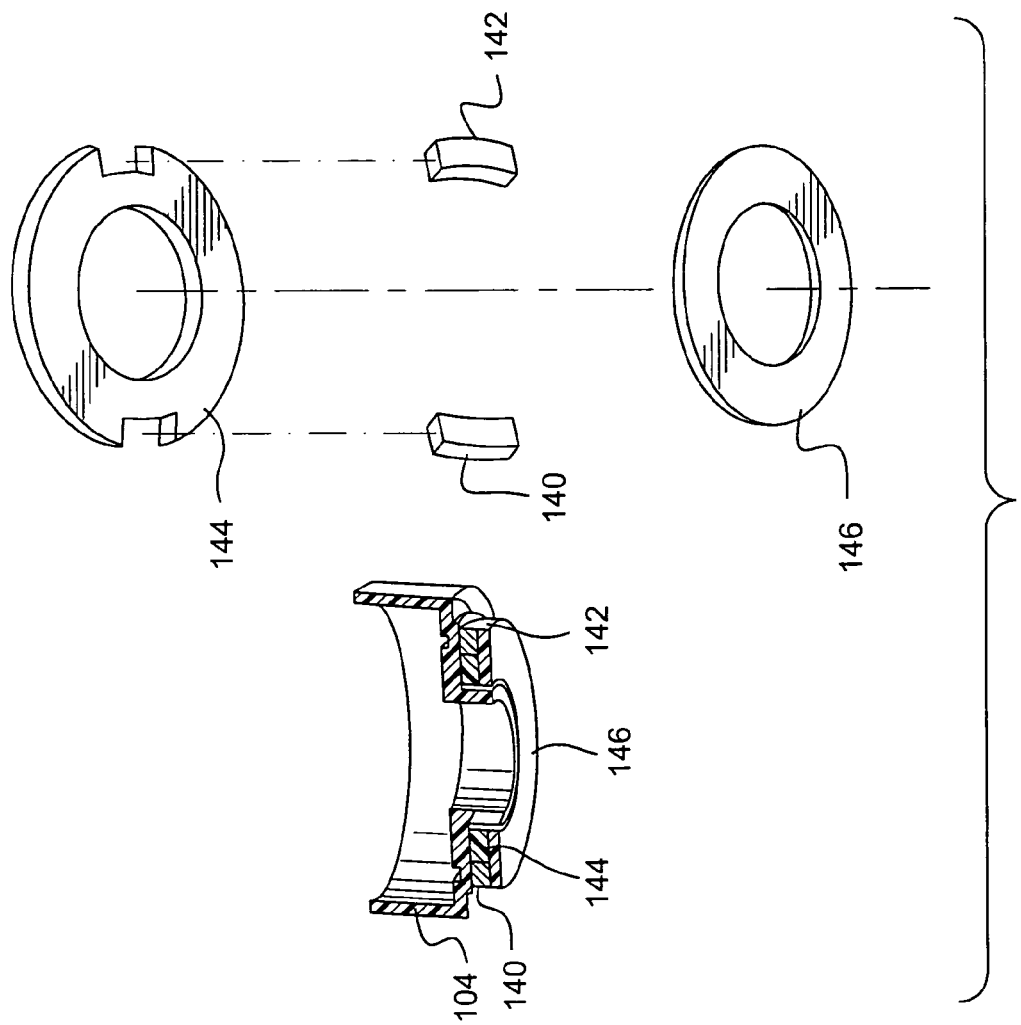
FIG. 6B
FIG. 6A

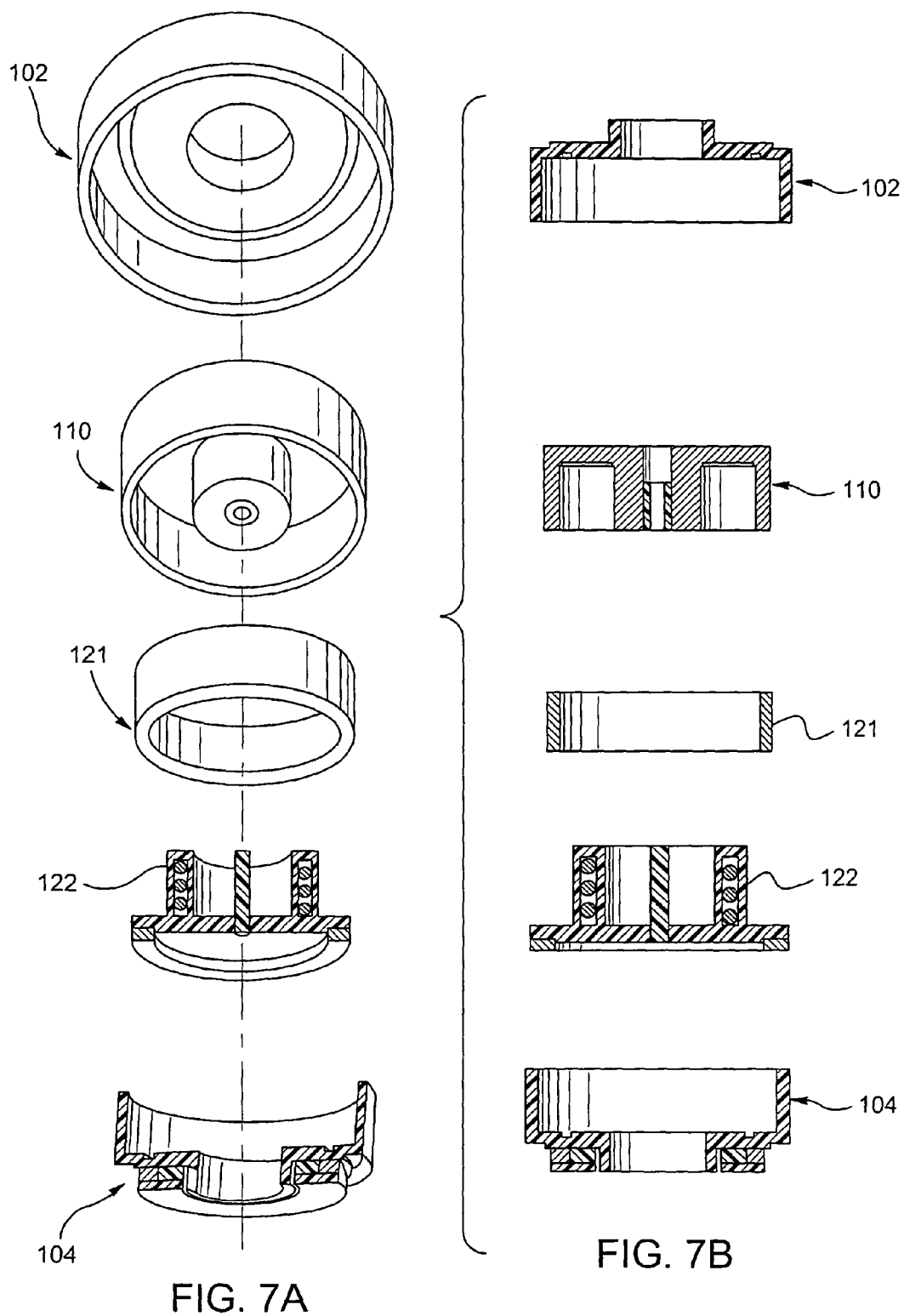

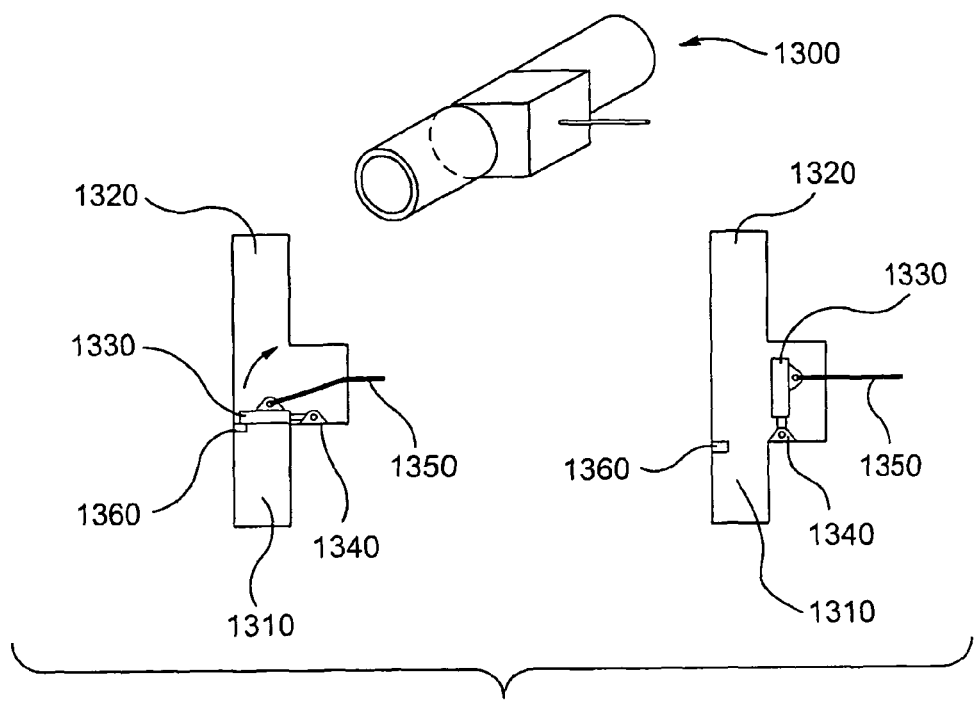
FIG. 13
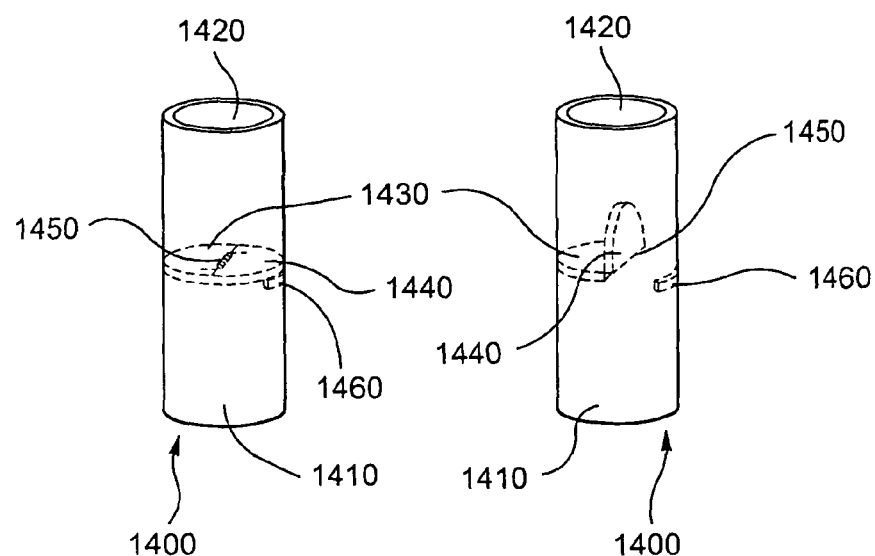
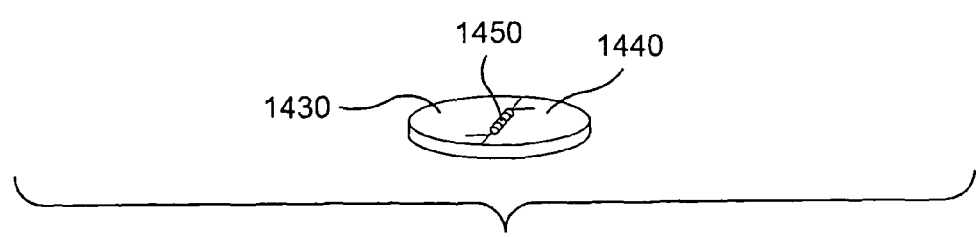
FIG. 14

METHOD AND APPARATUS FOR BACKSPILL PREVENTION

CROSS REFERENCE TO APPLICATIONS

This application claims the benefit of U.S. Provisional Patent No. 60/996,159, filed Nov. 5, 2007, incorporated by reference in its entirety.

TECHNOLOGICAL FIELD

The technology herein relates to a method and apparatus for backspill prevention. More particularly, the technology herein relates to a method and apparatus for positive airway pressure (PAP) device backspill prevention using a controlled backspill prevention apparatus.

BACKGROUND AND SUMMARY

PAP devices are designed for portable use and aid in the treatment of sleep apnea. Using pressurized air delivered through, for example, a face-mask, they force a patient's airways open, allowing unobstructed breathing during sleep.

In addition to delivering pressurized gas into one or more of the patient's airways, PAP devices can be connected to or otherwise provided to other useful accessories, such as a humidifier. The humidifier can even be included as a part of the device. For example, it can be provided in the form of a small chamber housed therein. In either case, the humidifier typically includes a supply of water (e.g., up several hundred milliliters).

While such a combination is convenient for the patient, it does suffer from some potential drawbacks. For example, the tube by which the humidified gas is provided to the patient is also in communication with the fan or blower motor, either directly or indirectly. Unfortunately, the fan or blower is typically not waterproof, and if too much moisture or water contacts the fan or blower motor, some or all of the PAP device can be destroyed and/or a short circuit can occur. Since the humidifier and motor often communicate through the same air passageway, this backspill is a regularly occurring problem.

In normal, intended use, such arrangements do not present a problem, as the device is designed such that water from the humidifier chamber does not flow back down the air passageway and into the fan or blower housing. Problems arise, for example, when the device is turned off and being transported from one place to another. The person carrying the machine may not even be aware of a need to keep it oriented in a certain position, or they may not be aware that water has a potential to leak or splash from the humidifier into the fan motor. If the machine is improperly or carelessly carried and backspill water reaches the fan motor, when the machine is next activated, the motor may short out or be destroyed entirely, resulting in a costly repair bill or perhaps the need to replace the entire device.

The exemplary illustrative non-limiting implementations herein provide a device which can be fit within a PAP device and which prevents such a backspill from occurring by sealing the air passageway when the machine is turned off for transportation.

According to one exemplary illustrative non-limiting implementation, a first magnet is housed within a chamber and has a magnetic field oriented substantially towards a hollow center thereof and an outer edge thereof. A solenoid interfaces with the hollow center of the magnet and is further provided with a backspill stop that includes some amount of magnetically attractable material. One or more second magnets are also provided to the housing, having magnetic fields directed towards the backspill stop. The second magnets are situated generally near the outside of an opening in the housing, and the magnets function to hold the backspill stop in place against the housing, blocking the opening. When the solenoid is activated, it interacts with the radial magnetic field of the first magnet to pull the backspill stop away from the opening as the solenoid is drawn through the magnetic field in a direction away from the opening.

In a further exemplary illustrative non-limiting implementation, the solenoid/backspill stop combination is built into a PAP or other device as part of the assembly process thereof (e.g., it is a part of the air passageway, housed in a chamber larger than the passageway that it is intended to restrict). In another exemplary illustrative non-limiting implementation, the solenoid/backspill stop combination is housed in a connecting piece that can be inserted between two passageways at a desired location.

In still another exemplary illustrative non-limiting implementation, other controllable backspill prevention mechanisms are used to block and unblock a passageway in a PAP device. These exemplary backspill prevention implementations allow air passage in a first position and block the passageway in a second position.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings:

FIG. 1D shows the cross section of FIG. 1B with the exemplary solenoid backspill prevention apparatus in a closed position;

FIG. 2A shows a perspective view of a portion of an exemplary housing first portion according to an example of the present invention;

FIG. 2B shows a cross section of the housing first portion of FIG. 2A;

FIG. 4A shows a perspective view of an exemplary cylindrical magnet according to an example of the present invention;

FIGS. 4B and 4C show, respectively, a cross section and a top view from above of an exemplary cylindrical magnet;

FIG. 5A shows an exploded perspective view of an exemplary engaging solenoid including a backspill stop, an exemplary ring of magnetically attractable material, and an exemplary guide shaft according to an example of the present invention;

FIG. 5B is an assembled view of an the exemplary engaging solenoid of FIG. 5A;

FIG. 6A shows an exploded perspective view of an exemplary housing second portion, an exemplary magnet positioning ring, exemplary magnetic material, and an exemplary retaining ring according to an example of the present invention;

FIG. 6B shows an assembled view of the exemplary housing second portion of FIG. 6A;

FIG. 7A shows a perspective view of an exploded exemplary solenoid backspill prevention apparatus according to an example of the present invention;

FIG. 7B shows a cross-sectional view of the exploded exemplary solenoid backspill prevention apparatus of FIG. 7A;

FIG. 13 shows an exemplary hinged-gate backspill prevention apparatus according to an example of the present invention;

FIG. 14 shows an exemplary one-way hinged-gate backspill prevention apparatus according to an example of the present invention;

DETAILED DESCRIPTION OF ILLUSTRATED EMBODIMENTS

The following description is provided in relation to several embodiments which may share common characteristics and features. It is to be understood that one or more features of any one embodiment may be combinable with one or more features of the other embodiments. In addition, any single feature or combination of features in any of the embodiments may constitute additional embodiments.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The term "air" will be taken to include breathable gases, for example air with supplemental oxygen. It is also acknowledged that the blowers described herein may be designed to pump fluids other than air.

1.0 Exemplary PAP Device

Figure 1A:
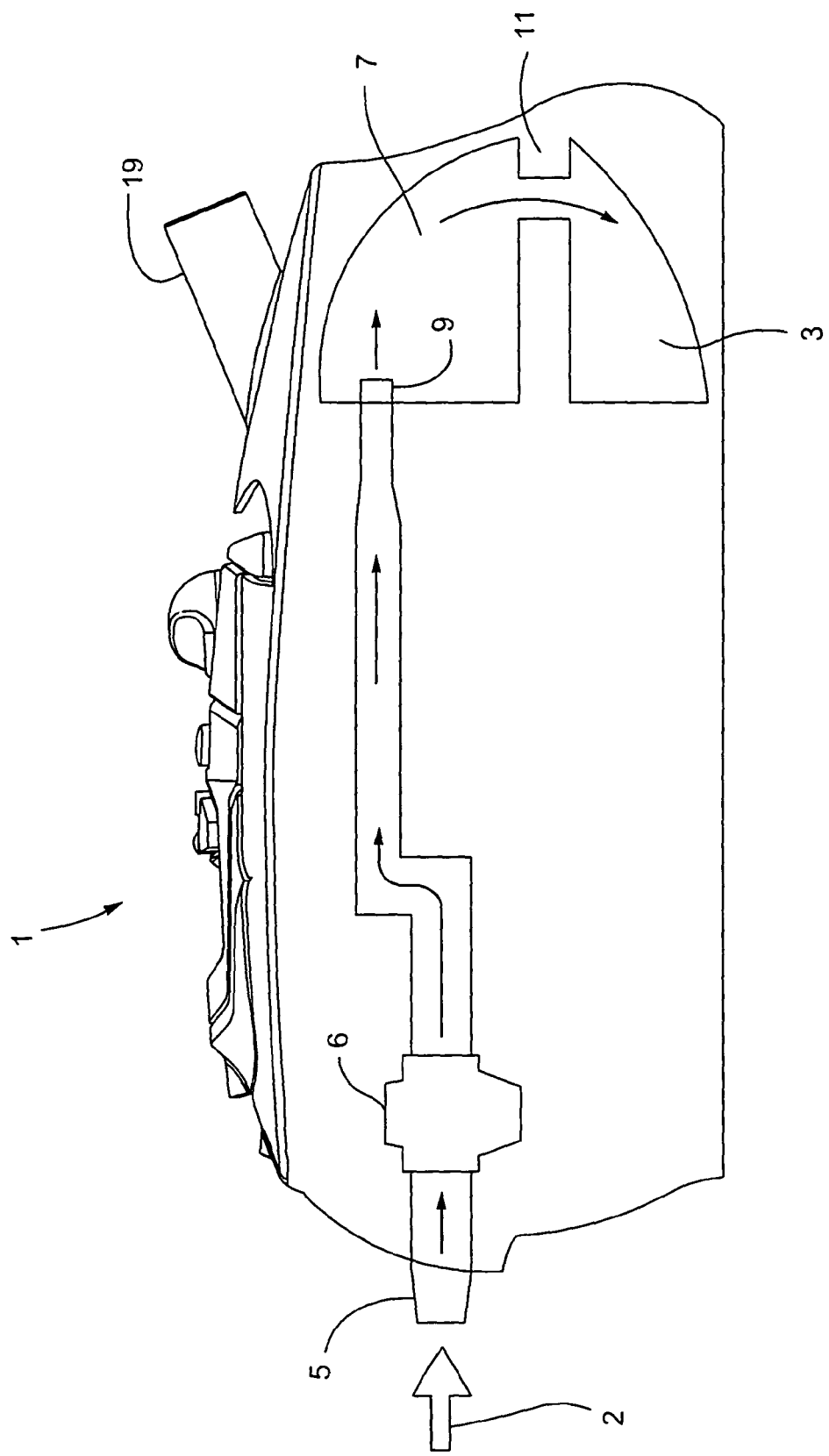
FIG. 1A shows an exemplary PAP device including a humidifier chamber according to an example of the present invention.

FIG. 1A shows an exemplary PAP device 1 provided with a humidifier chamber 3. When the device 1 is operated, motor 6 powers a fan to suck air 2 in through intake 5. After passing through the device 1 interior, the air 2 exits through entry connector 9 into pre-humidifier chamber 7.

The air 2 is then forced down humidifier entrance opening 11 into the humidifier chamber 3. Air pressure forces the air 2 up through exit 19.

If the PAP device is, for example, inverted, the water from humidifier chamber 3 can pour through humidifier entrance opening 11 into pre-humidifier chamber 7. This water can then pass through entry connector 9 and reach motor 6 inside the PAP device.

2.0 Exemplary Solenoid Backspill Prevention Apparatus

Figure 1C:
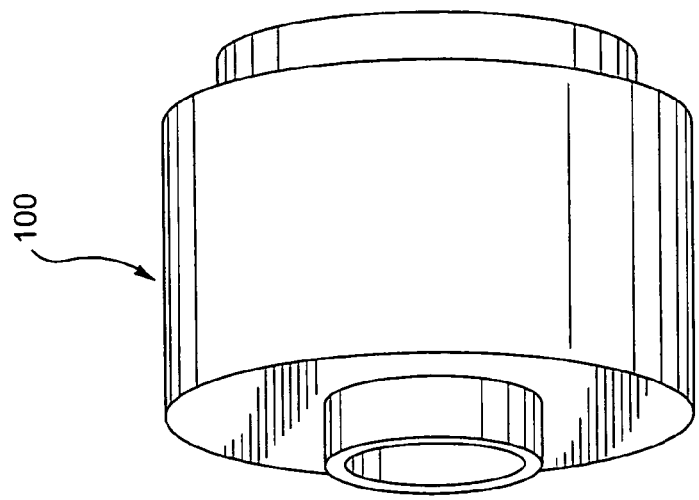
FIG. 1C is a perspective view of the exemplary solenoid backspill prevention apparatus of FIG. 1B.
Figure 1B:
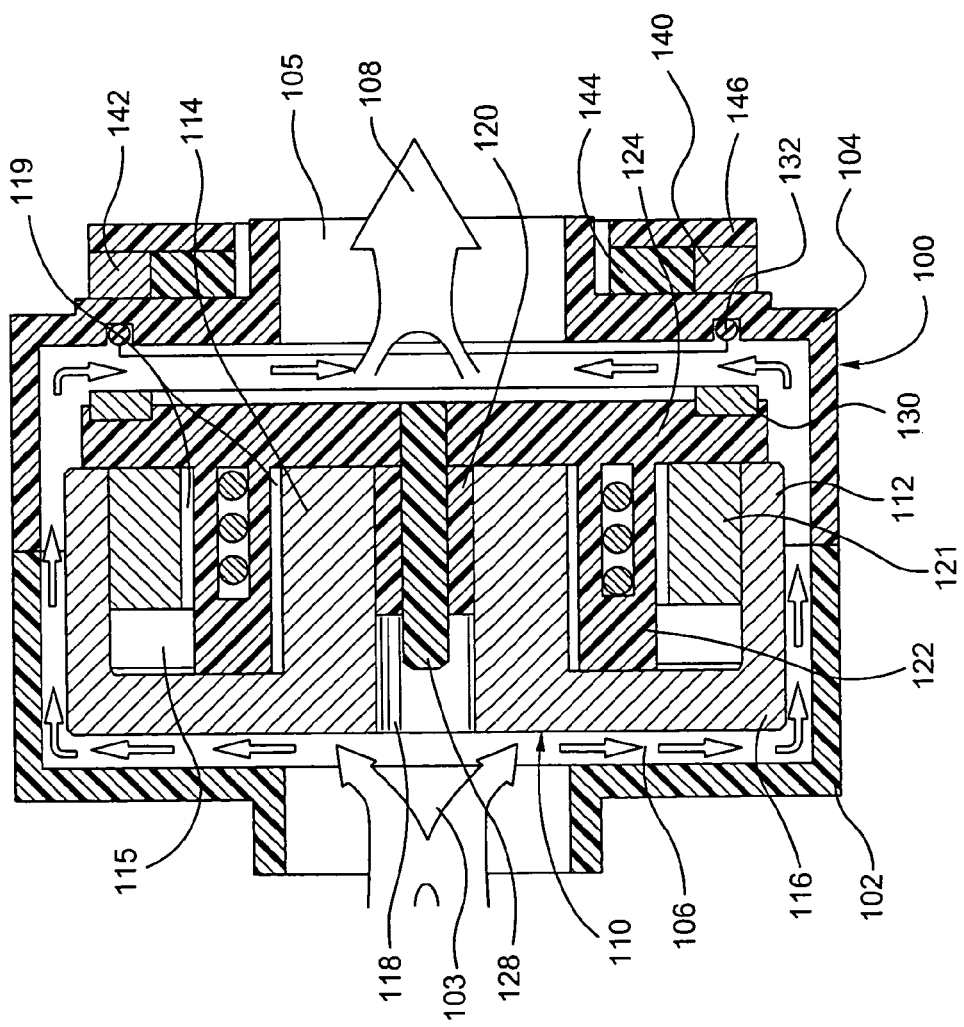
FIG. 1B shows a cross-section of an exemplary solenoid backspill prevention apparatus according to an example of the present invention.

FIG. 1B shows an exemplary solenoid backspill prevention apparatus 100 in cross-section. According to this exemplary illustrative non-limiting implementation, an apparatus housing 100 has a first portion 102 and a second portion 104. The two housing portions 102, 104 define a chamber 106 which houses much of the remaining apparatus and through which air 108 can flow. According to this implementation, each housing portion 102, 104 is provided with a respective opening 103, 105 through which air can pass into and out of the central chamber 106.

In addition to air 108 flowing through the chamber 106, in this implementation a receiving cylinder 110 is included in the apparatus 100. The cylinder has an outer wall 112 and an inner wall 114 connected by a closed end 116 and separated by hollow portion 115. According to this illustrative implementation, the closed end 116 has a guide hole 118 provided therethrough, which extends the length of the inner cylinder 114 wall. While there is a single, centrally located guide hole in this implementation, a plurality of guide holes, provided at suitable locations could also be used, or guide holes could be excluded from the apparatus entirely.

In this illustrative implementation, there is also a linear bearing 120 provided to the guide hole 118. The bearing 120 has a hollow center through which a guide shaft 128 can pass. Guide holes could also be provided without linear bearings, and the guide shafts could interface directly with the guide holes.

According to this illustrative implementation, a cylindrical first magnet 121 is arranged generally inside the hollow portion 115 of the receiving cylinder 110. The cylindrical first magnet in this implementation is shaped like a ring, and a hollow center of the magnet 121 has a greater diameter than the inner wall 114 such that a gap 119 exists between the hollow center and the inner wall 114.

In this illustrative implementation, the gap 119 is large enough to allow passage of an engaging solenoid 122. At one engaging solenoid end is a backspill stop 124. Since this backspill stop 124 will be covering the opening 105 in the housing when the apparatus is closed, it has a diameter greater than that of the opening 105. The backspill stop is also provided with at least one piece of magnetically attractable material 130, which in this implementation is in a ring shape. The magnetically attractable material 130 shape is not critical, but at least some portion of the magnetically attractable material 130 should be in a position such that it is attracted to magnets 140, 142 when the solenoid is not powered. Magnets 140, 142 could also be provided as a single magnetic ring.

Additionally, in this exemplary implementation, the backspill stop 124 has the guide shaft 128 mounted in the center thereof that interfaces with the linear bearing 120.

According to this illustrative implementation, an o-ring 132 is seated opposite the backspill stop 124 and surrounds the opening 105 in the second housing portion 104. While not necessary, the o-ring 132 can be provided to help create a tight seal when the backspill stop 124 is in a closed position.

In this implementation, the two magnets 140, 142 are positioned on either side of the opening 105 and held in place by a magnet positioning ring 144 and a retaining ring 146. The magnets are arranged such that their magnetic field creates a pull on the magnetically attractable material 130. This pull is great enough to pull the backspill stop 124 into sealing contact with the o-ring 132 when the solenoid is not powered, thus sealing off the opening 105 from backspill of water. When the solenoid is powered, however, it creates a stronger pull away from the opening 105 than that of the magnets 140, 142 and pulls the backspill stop 124 away from the o-ring 132 allowing air to again pass through the opening 105.

According to one implementation, the solenoid is powered when the PAP device is powered, such that as long as the PAP device is powered, the solenoid holds the backspill stop open. Other configurations are contemplated as well. For example, the solenoid could be placed in the position shown in the figures, but only be powerable in the absence of water in the vicinity of the backspill stop. Water detection can be performed by a number of known methods, such as providing a plurality of contacts to the passageway and detecting if a connection between any of the contacts is made (which would occur in the presence of, for example, water).

FIG. 1C shows a perspective view of an assembled exemplary solenoid backspill prevention apparatus 100. In this exemplary illustrative non-limiting implementation, the apparatus is provided as a connecting piece which can be inserted between two passageways, such as two lengths of tubing. It is also contemplated that the solenoid backspill prevention apparatus may be provided in a variety of fashions, such as being included in the assembly of a device (as opposed to being a removable piece), being included as a part of a larger removable piece, etc.

FIG. 1D shows the solenoid backspill prevention apparatus of FIG. 1B. In this exemplary illustration, the backspill stop 124 has moved into a sealing arrangement with O-ring 132. This arrangement prevents air and water from moving past the backspill stop 124.

2.0.1 Exemplary First Housing Portion

FIGS. 2A and 2B show perspective and cross-sectional views of an exemplary first housing portion 102. In this illustrative exemplary non-limiting implementation, the first housing portion comprises a first cylindrical wall 202 having a partially closed end and an open end. The partial closure is created by disk 204 having an opening 103 in the center thereof. The opening 103 is further ringed by a second cylindrical wall 206. Although the shapes of the exemplary implementation are described in the examples as being cylindrical, they could be made in any shape suitable for a particular application.

2.0.2 Exemplary Receiving Cylinder

Figure 3B:
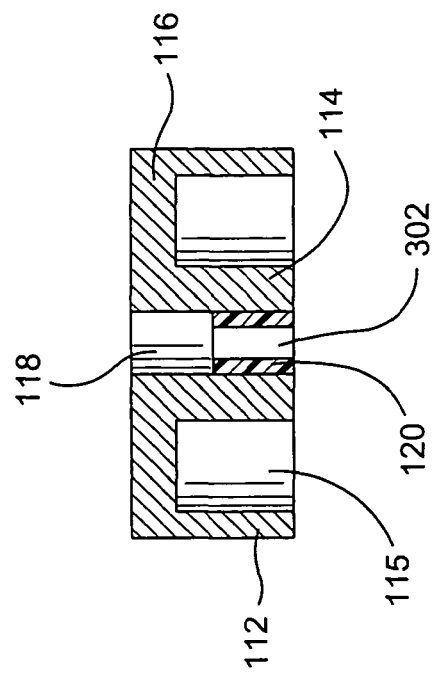
FIG. 3B is a cross-sectional view of the exemplary receiving cylinder and exemplary linear bearing of FIG. 3A.
Figure 3A:
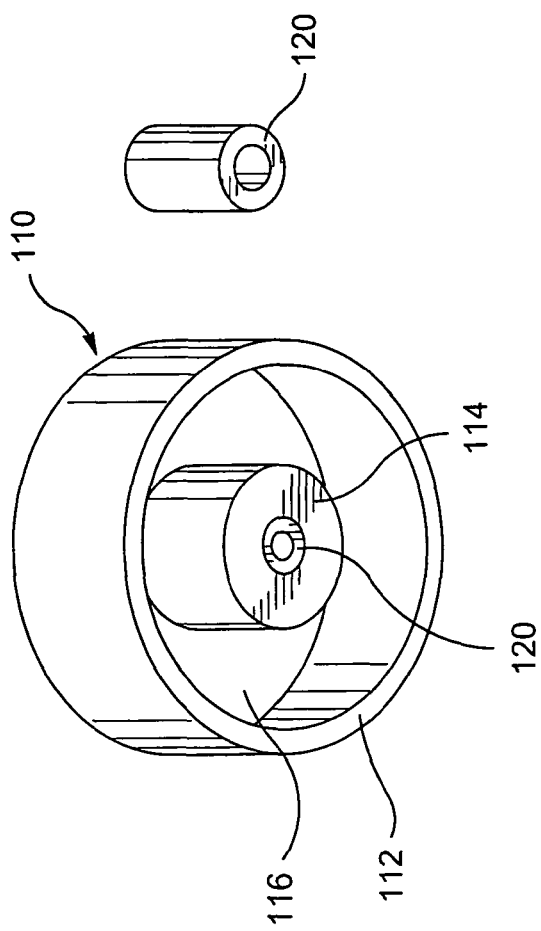
FIG. 3A shows a perspective view of an exemplary receiving cylinder and an exemplary linear bearing according to an example of the present invention.

FIGS. 3A and 3B show different views of an exemplary receiving cylinder 110. The exemplary receiving cylinder has a plurality of cylindrical walls 112, 114 provided thereto and joined by a disk 116. In this exemplary illustrative non-limiting implementation, the inner cylindrical wall 114 has an additional bore down the center thereof and passing through the disk 116, creating guide hole 118.

According to this illustrative implementation, the guide hole 118 is further provided with linear bearing 120. The linear bearing 120 has a hollow core 302 to allow insertion of the guide shaft (128, FIGS. 5A and 5B) provided to an engaging solenoid.

Between the cylindrical walls 112, 114 is a hollow area 115 adapted for receiving both a cylindrical magnet (121, FIGS. 4A and 4B) and an engaging solenoid (122, FIGS. 5A and 5B). When the solenoid activates, it creates a magnetic field, which interfaces with a radial magnetic field of the cylindrical magnet, drawing a backspill stop portion (124, FIGS. 5A and 5B) of an engaging solenoid, provided with a magnetically attractable material (130, FIGS. 5A and 5B), away from an opening. The interaction between the solenoid field and the radial field also pushes the engaging solenoid guide shaft to upwards into the guide hole 118. In this way, the engaging solenoid is kept in alignment with the receiving cylinder so that the solenoid backspill prevention apparatus can continue to operate properly.

While the configuration shown functions to keep the engaging solenoid and the receiving cylinder aligned, a variety of configurations and shapes performing the same function can be implemented without departing from the scope of the present invention. The particular configuration shown herein is for exemplary purposes only.

2.0.3 Exemplary Cylindrical Magnet

FIGS. 4A and 4B show a plurality of views of an exemplary cylindrical first magnet 121. In this exemplary illustrative non-limiting implementation, the solenoid is generally ring shaped and has an outer diameter that is smaller than an inner diameter of the receiving piece's outer cylinder wall 112. This allows the magnet 121 to fit within the hollow portion 115 of the receiving cylinder.

According to this implementation, the cylindrical magnet 121 is formed of six pieces of magnet, fused together, having alternating field orientation. The fields of the magnets are further aligned radially, so that the field is focused at least towards the center of the cylinder. When a solenoid provided at least partially within the cylinder is activated, the field generated by the solenoid causes the solenoid to be drawn through the center of the cylinder as the solenoid field interacts with the radial field. The pieces of magnet, which can also be more or less than six, as is suitable for a particular application, can also be pressed together, glued together, or held together by any other suitable means.

According to this implementation, the force generated by the solenoid being drawn through the radial magnetic field must be great enough to overcome a magnetic force applied to a piece of magnetically attractable material (130, FIGS. 5A and 5B) by second magnets (140, 142, FIGS. 6A and 6B).

The amount of force that the solenoid must generate is at least partially dependent on the strength of the magnets 140, 142 opposite the solenoid. For example, the stronger the magnets, the more force the solenoid will have to generate, since the magnetic force generated to be overcome by the solenoid will be greater.

2.0.4 Exemplary Engaging Solenoid

FIGS. 5A and 5B show views of an exemplary engaging solenoid 122. According to this exemplary illustrative non-limiting implementation the wall of the solenoid 122 serves as a guide to keep the engaging solenoid 122 properly aligned. Resultantly, it is thin enough and has the appropriate diameter to fit between an inner diameter of the cylindrical magnet 121 and outer diameter of the receiving cylinder's inner cylindrical wall 114. This configuration allows the engaging solenoid to move freely while maintaining its alignment.

According to this exemplary implementation, the solenoid comprises a wound piece of wire wrapped about a cylinder and creating an electromagnet. Some parameters for an exemplary solenoid coil are given below for illustrative purposes only, and are not intended to limit the scope of the invention in any way and in fact may be varied up to ±20% of the exemplary values shown below:

| Parameter | Unit | Value |
| --- | --- | --- |
| Coil one side dimensions | mm | 65.17 |
| Filling Factor | | 0.45 |
| Current Density | A/mm$^2$ | 5.5 |
| Ampere turns | | 161.295 |
| Coil Current | A | 0.5 |
| Number of turns | | 322.59 |
| Number of turns (rounded) | | 323 |
| Average Coil Diameter, | mm | 24.3 |
| Average Turn Length, | mm | 76.341 |
| Total Wire Length | mm | 24658.0 |
| Single Wire Area | mm$^2$ | 0.091 |
| Wire Diameter, | mm | 0.340 |
| AWG | | 27.5 |
| Coil Resistance | Ohm | 4.676 |
| Coil Voltage | V | 2.338 |
| Coil Power at Steady State | W | 1.169 |

In this exemplary implementation, a backspill stop 124 is provided at one end of the engaging solenoid. This backspill stop 124 acts as the valve that seals off the passageway 105, and has a greater diameter than the passageway 105. At least one piece of magnetically attractable material 130 is also provided to the backspill stop.

According to this exemplary implementation, the piece of magnetically attractable material is a ring 130, however it could be several pieces, a solid disk, etc. The ring 130 is positioned such that it can be attracted by a field generated by the second magnet(s) 140, 142. An exemplary ring 130 positioning places it within a groove 502 cut in the bottom of the disk. The groove 502 is cut to have a diameter that places at least portions of the groove in lateral alignment with the magnetic material 140,142 when the apparatus is assembled. Regardless of the form in which the magnetically attractable material is provided, the only limits on its positioning are that it should be attractable by magnetic fields from the magnetic material 140, 142.

Additionally, in this implementation the magnetically attractable material 130 is shown as being provided on a first face of the backspill stop 124, but the material 130 could also be embedded in the backspill stop 124, the backspill stop 124 could be comprised of the material 130, or the material 130 could be on a different face of the backspill stop 124.

In this exemplary implementation, the backspill stop 124 also has a central hole 504 provided therein into which a guide shaft 128 can be placed. The guide shaft 128 is designed to interface with a linear bearing 120, although it can additionally simply interface with a guide hole 118. Also, the shaft need not be centered, nor is it a requirement that there be only one shaft. If a plurality of guide holes are present then a plurality of guide shafts may be present. Conversely, if no guide holes are present, then the guide shafts may be excluded altogether. In this implementation, the guide shaft 128 helps to keep the engaging solenoid 122 in proper alignment to maintain backspill stop functionality.

2.0.5 Exemplary Second Housing Portion

FIGS. 6A and 6B show views of an exemplary second portion of a solenoid backspill prevention housing 104 having an opening 105 therein. Two magnets 140, 142 are provided at the general outside diameter of the opening 105, although in this implementation there is a magnet positioning ring 144 interposed between the opening 105 and the magnets 140, 142. A retaining ring 146 holds the magnets and the positioning ring in position against the second housing portion 104, and may further be part of the magnetic circuit. The retaining ring is made from soft magnetic material having high permeability in one exemplary implementation.

The magnets 140, 142 are positioned such that they are in general lateral alignment with at least a portion of the magnetically attractable material 130. Additionally the magnets should be strong enough to pull the engaging cylinder 122, including the backspill stop 124 and magnetically attractable material 130 into a closed position from an open position. This generally means that the larger the gap between the magnets 140, 142 and the attractable material 130, the stronger the magnets will have to be. The magnets might also need to be strong enough to hold the backspill stop 124 in position with some amount of pressure being applied to the backspill stop from the side of the opening 105. For example, if the solenoid backspill prevention apparatus was implemented in a PAP device, then if the patient tilted the device improperly and spilled water down the air passageway while the solenoid was turned off, the magnets 140, 142 might need to be strong enough to hold the backspill stop 124 in a closed position against water pressure and prevent water from reaching the fan.

Further, the magnets 140 and 142 may be installed in the way that their directions of magnetization are opposite to each other in one exemplary implementation. For instance, if the surface of the magnet 140 which interfaces with the retaining ring 146 has the direction of the North Pole magnetization, the similar surface of the magnet 142 has the South Pole direction.

While an exemplary positioning of two magnets is shown for illustrative purposes, it is contemplated that a variety of positionings and one or several magnets could be used. For example, a single magnet could be placed directly against the outer wall of the opening 105 or three or four magnets could be spaced periodically therearound. Any configuration rendering the backspill stop operational can be used.

2.1 Exemplary Solenoid Apparatus (Exploded View)

FIGS. 7A and 7B show exploded views of an exemplary solenoid backspill prevention apparatus. Outer portions 102, 104 form the housing for the apparatus, holding receiving cylinder 110, cylindrical magnet 121, and engaging solenoid 122 thereinside. Receiving cylinder 110 and engaging solenoid 122 align and are provided with cylindrical magnet 121 interposed therebetween.

3.0 Exemplary Solenoid Backspill Prevention Apparatus Provided to a PAP Device

Figure 8:
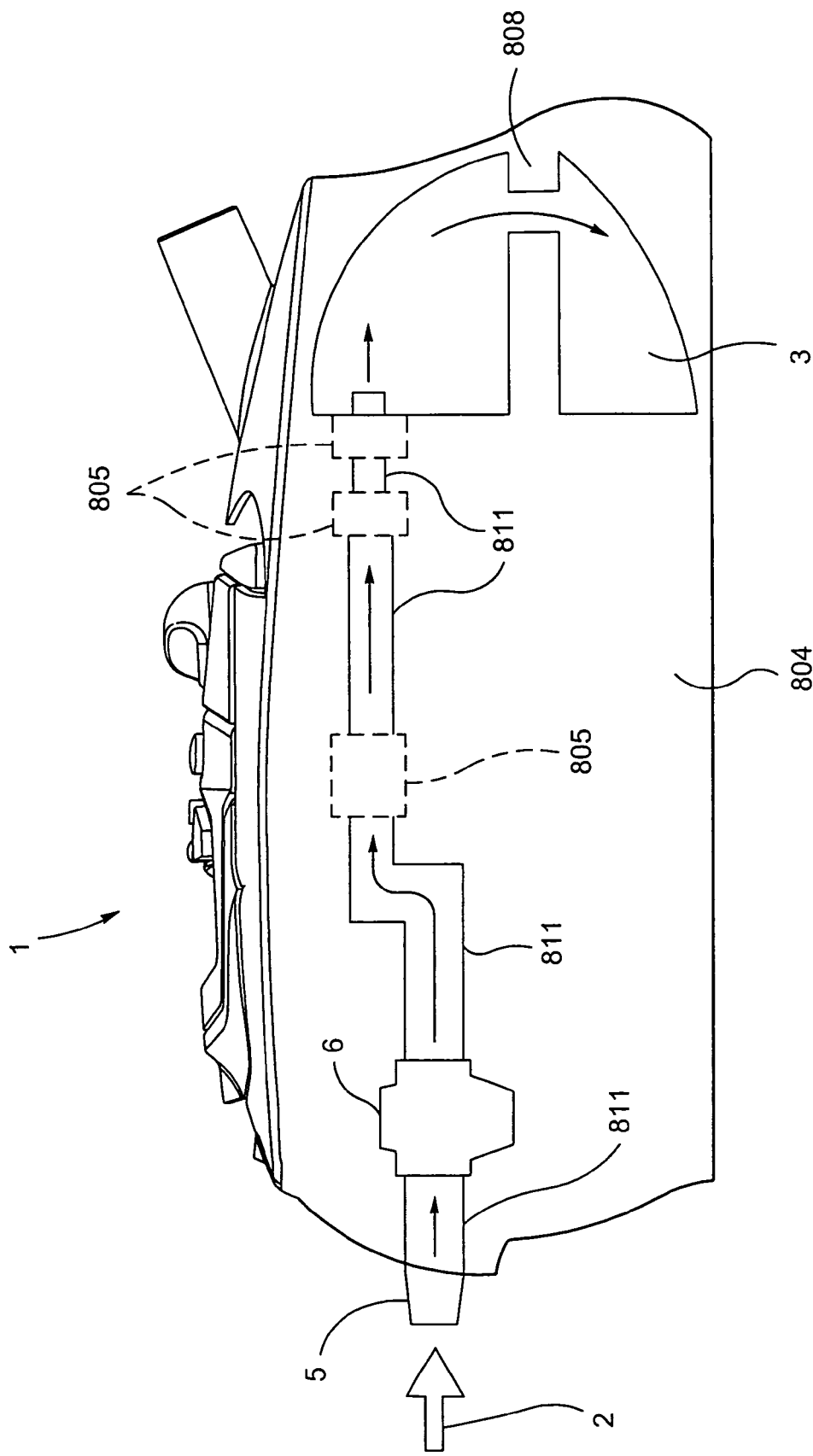
FIG. 8 is a schematic view of an exemplary solenoid backspill prevention apparatus provided to an exemplary PAP device according to an example of the present invention.

FIG. 8 shows an exemplary schematic of an exemplary solenoid backspill prevention apparatus provided to an exemplary PAP device 1. Air 2 enters through intake 5 and moves into passageway 811. The air 2 is sucked in by motor 6 powering a fan and then forced further down passageway 811.

The motor 6 is not protected from water and can be damaged if water comes in contact with it, so the solenoid backspill prevention apparatus 805 should be positioned between the motor 6 and a humidifier tank 3.

The solenoid backspill prevention apparatus 805 may be placed within the PAP device housing 804, between the PAP device housing 804 and the humidifier housing 808, or within the humidifier housing 808. In any of those placements, the apparatus 805 can prevent water from escaping from the tank 3 and moving back into the passageway 811 to contact the motor 6.

Additionally, the PAP device can be provided with a button, switch or similar mechanism that allows a person carrying the PAP device to indicate that the device is being transported. For example, upon activation of the transport indicator, the backspill prevention apparatus could move to a sealing arrangement (e.g. as shown in FIG. 1D), thus preventing backspill of water while the device is in transit.

Alternatively, or additionally, the PAP device could be provided with one or more movement or orientation sensors, such as a mercury switch. The sensor(s) could be arranged so that, in certain orientations, the switch(es) are triggered. For example, if the device was inverted, turned sideways, or placed in any other orientation in which water was likely to leak out of the humidifier chamber, the switch(es) could cause the backspill prevention apparatus to seal the air passageway.

The PAP device could also be provided with moisture sensors that sense the presence of any water in the passageway in the region of the backspill prevention apparatus. Alternatively, these sensors could be configured such that a minimum amount of water must be present in order to trigger the moisture sensors. Upon detection of any or a specified minimum amount of water, the sensors could cause the backspill prevention apparatus to seal the air passageway.

4.0 Exemplary Alternative Solenoid Backspill Prevention Apparatus

Although a specific solenoid backspill prevention apparatus has been presented herein for exemplary purposes, it is contemplated that a variety of different configurations of solenoid backspill prevention apparatus could be used to block/unblock a passageway of a PAP device. FIGS. 9A-9E present a non-exhaustive set of examples of further solenoid backspill prevention apparatus which could perform substantially the same functionality.

Figure 9A:
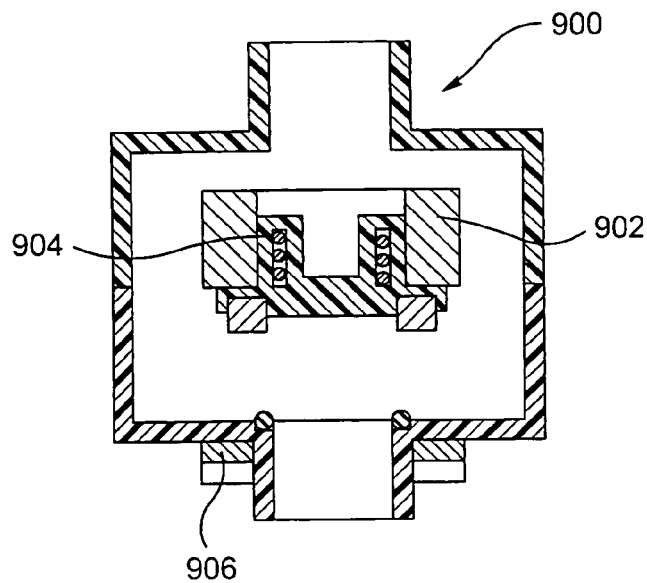
FIGS. 9A-E show various exemplary implementations of additional solenoid backspill prevention apparatuses according to examples of the present invention.

The solenoid backspill prevention apparatus 900 in FIG. 9A includes a backspill stop similar to the one shown in FIGS. 1-7, except here an inner cylinder of magnet 902 receives engaging solenoid 904. There is no receiving cylinder presented in this embodiment, rather the cylinder of engaging solenoid 904 fits within the center diameter of magnet 902. Magnets 906 are provided in generally the same place as the magnets 140, 142 from FIGS. 7A and 7B.

Figure 9B:
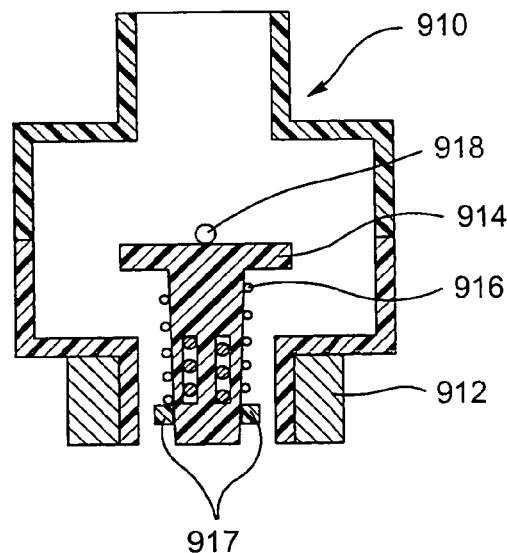

Another solenoid backspill prevention apparatus 910 in FIG. 9B uses a similar engaging solenoid 914, but no oppositional magnets. Instead, the magnet 912 is provided to the outer housing portion and, when the solenoid 914 is powered, a housing opening is sealed. When the solenoid 914 is not powered, a spring 916 biases the engaging solenoid into an open position and unseals the opening. Supports 917 hold the engaging solenoid and spring in place and stop 918 prevents the engaging solenoid from moving past a predetermined position.

Figure 9C:
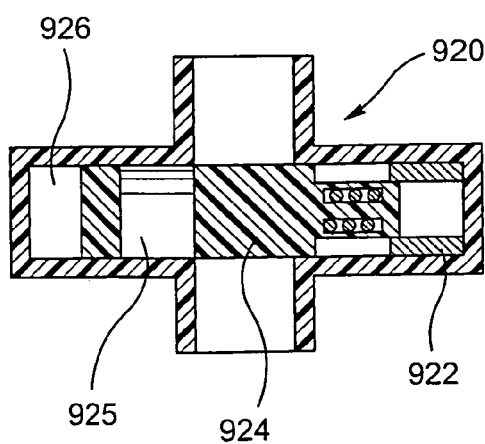
Figure 9D:
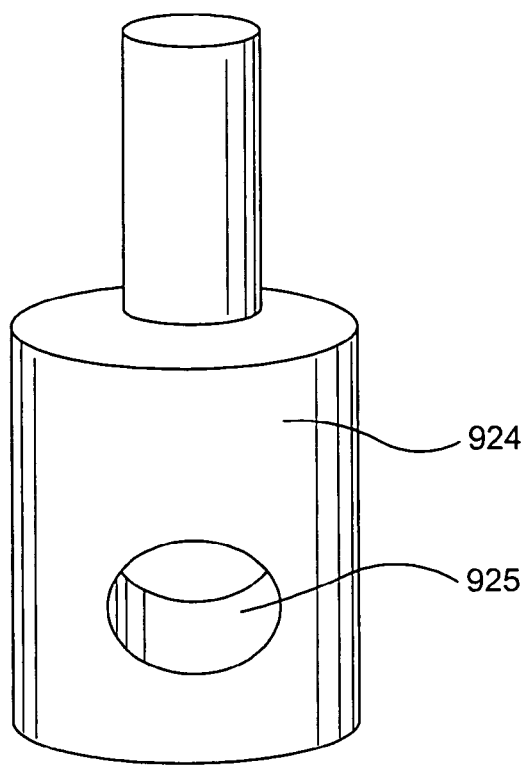

Still a further solenoid backspill prevention apparatus 920 in FIGS. 9C and 9D has an entirely different engaging solenoid 924, provided with a passageway 925 therethrough. Solenoid 924, when powered, interfaces with magnet 922 to pull the engaging solenoid into a position such that passageway 925 aligns with openings in the housing, allowing passage therethrough. When the solenoid is not powered, magnet 926 pulls the engaging solenoid 925 into a position such that passageway 925 is no longer aligned with an opening in the housing, preventing flow therethrough.

Pieces similar to those shown in FIGS. 9C and 9D could be used to create an additional exemplary backspill prevention apparatus that does not use a solenoid. Engaging device 924 could be spun about a radial axis such that when in a first position the passageway 925 aligns with openings in the housing and when in a second position the passageway is rotated 90° from alignment, preventing passage of water therethrough. This spinning could be done through a manual control or a motorized control.

Figure 9E:
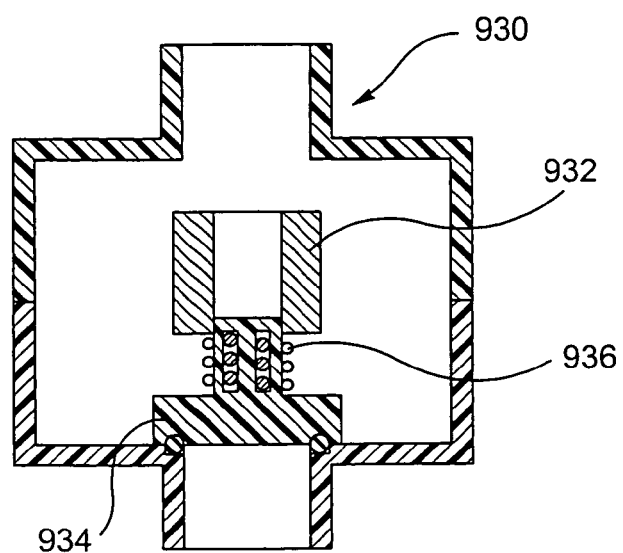

Yet another solenoid backspill prevention apparatus 930 in FIG. 9E shows a similar principal to the apparatus of FIGS. 1-7, wherein a powered engaging solenoid 934 holds a backspill stop provided to an engaging solenoid 934 in an open position. Here, however, like apparatus 900, the receiving cylinder is not included in the assembly. Additionally, instead of oppositional magnets that move the backspill stop into a closed position, a spring 936 acts to bias a backspill stop in a closed position over an opening. The force generated by the solenoid 934 interacting with the cylindrical magnet 932 must be sufficient to overcome the oppositional force of the spring to pull the engaging solenoid 934 into an open position.

While a variety of exemplary implementations have been provided in conjunction with FIGS. 9A-9E, they are intended for illustrative purposes only, and not intended to limit the scope of the invention in any way. A variety of backspill stop/solenoid combinations and configurations are possible without departing from the scope of the present invention, which is to be defined by the claims.

5.0 Additional Exemplary Backspill Prevention Apparatus for Use in a PAP Device

Additionally, while the use of a solenoid backspill prevention apparatus as a mechanism for opening and closing a passageway provided in a PAP device has been discussed in detail herein, it is appreciated that a variety of mechanisms could be employed in a PAP device to achieve similar results. A non-exhaustive set of exemplary backspill prevention apparatus is shown in FIGS. 10-14.

Figure 10:
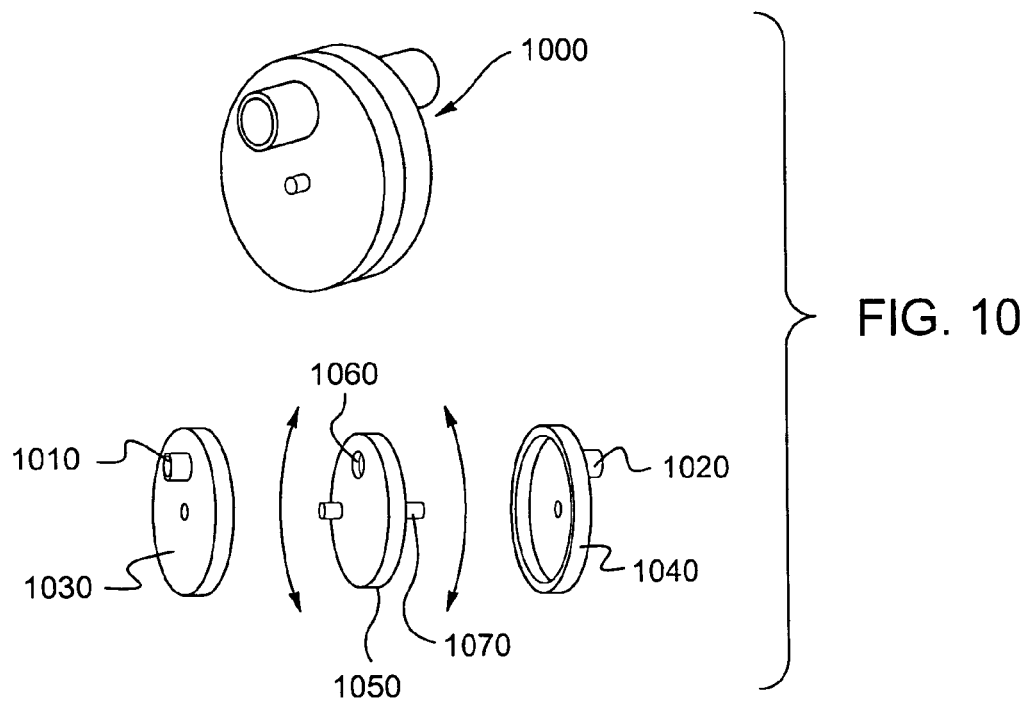
FIG. 10 shows an exemplary dial backspill prevention apparatus according to an example of the present invention.

FIG. 10 shows an exemplary dial mechanism 1000 that can be used to prevent the flow of undesired material down a passageway when in a first position and that can allow the passage of desired air when in a second position. Dial 1050 rotates in the directions of the arrows shown about the axis defined by seating peg 1070. Housing faces 1030, 1040 combine to create a housing for dial 1050, and openings 1010, 1020 can connect a first and second part of a passageway on either side of the dial mechanism 1000.

When the dial 1050 is rotated in one position by rotating peg 1070, dial opening 1060 is substantially aligned with openings 1010 and 1020 creating a passageway all the way through the housing. When the dial 1050 is in another position, dial opening 1060 is moved out of alignment and the connection between openings 1010 and 1020 is blocked by the dial body 1050.

Various biasing mechanisms can be used to hold the dial 1050 in a closed position when the PAP device is not powered. A motor with a locking axle running through the seating peg 1070 could be used, and the motor could turn the dial to an open position and lock it in the open position when the PAP device is powered. Or the mechanism could be manually dialed and biased by, for example, a detent arrangement. Another example of a biasing mechanism could be a spring and lock, where the spring biases the dial 1050 in a closed position and when the machine is turned on, the dial 1050 is turned against the tension in the spring and locked into an open position by a second biasing mechanism. The dial 1050 is released when the machine is turned off and the spring returns the dial 1050 to a closed position.

Figure 11:
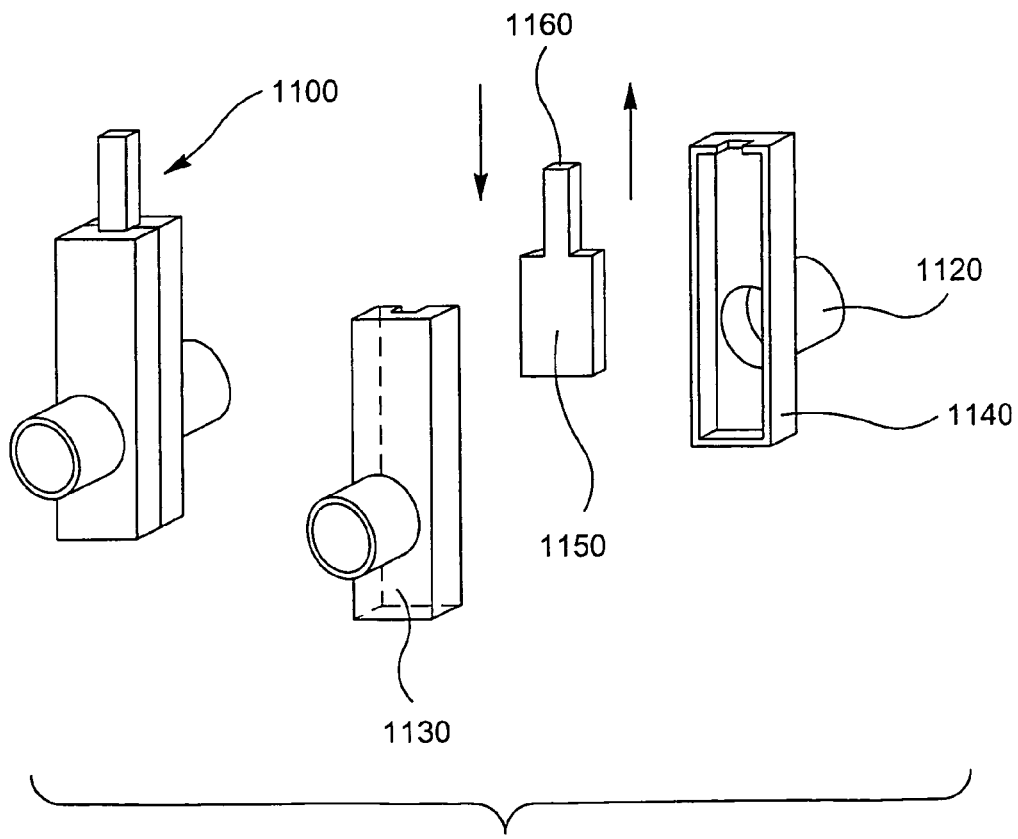
FIG. 11 shows an exemplary slidable gate backspill prevention apparatus according to an example of the present invention.

FIG. 11 shows an exemplary slidable gate divider 1100. In this exemplary illustrative non-limiting implementation, a slidable gate 1150 is secured between two housing halves 1130, 1140. Each housing half has an opening 1110, 1120 provided therein. Through use of, for example, a sliding tab 1160, the gate 1150 can be raised and lowered across the connection between the two openings 1110, 1120. When the gate is raised, air can flow freely between the two openings, when the gate is lowered, the passageway is blocked.

As with all of the exemplary illustrative non-limiting implementations provided herein, a variety of biasing mechanisms can be used to hold the gate in an open position when the PAP device is powered and a closed position when the PAP device is not powered.

Figure 12:
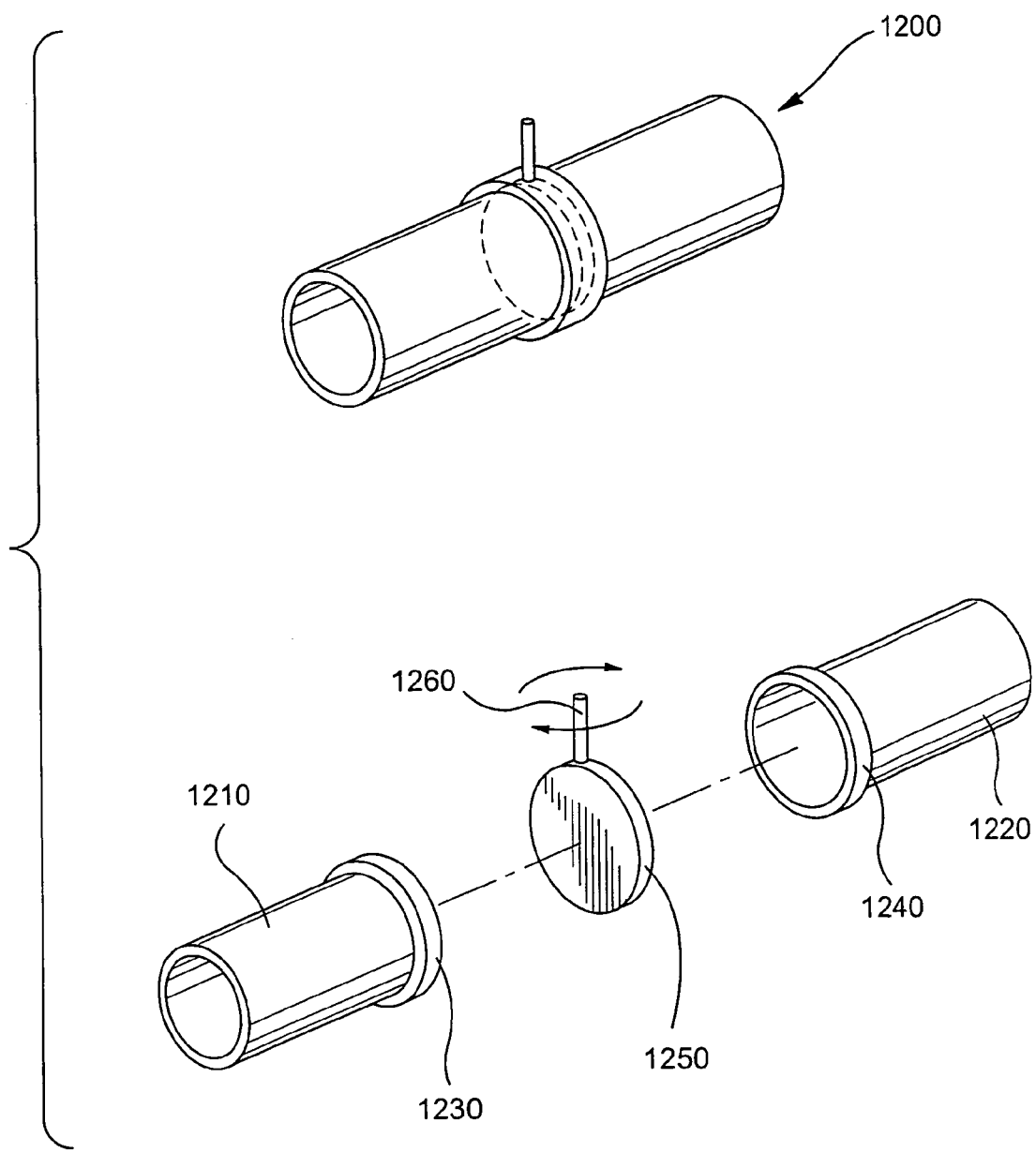
FIG. 12 shows an exemplary pivoting valve backspill prevention apparatus according to an example of the present invention.

FIG. 12 shows an exemplary pivoting valve divider 1200. In this exemplary illustrative non-limiting implementation, housing portions 1230, 1240 secure a pivoting valve 1250 between them. The valve 1250 is capable of pivoting about an axis running along a valve 1250 diameter. Openings 1210, 1220 are provided in each respective housing 1230, 1240 portion to allow passage of air through the housing.

When the valve 1250 is to be closed, it is pivoted such that a valve 1250 outer edge aligns with an passageway inner edge. The pivoting can be accomplished by turning the valve controller 1260. The valve then blocks the passageway and prevents air or other material from passing therethrough. When the valve needs to be opened, it is turned 90 degrees, for example, and the passageway is then unrestricted and air can pass freely therethrough. Again, a variety of biasing mechanisms can be employed to hold the valve in an open and a closed position.

FIG. 13 shows one exemplary hinged-gate divider 1300. The cross sections show the hinged gate 1330 in open and closed positions. When the hinged gate is biased in a closed position by a suitable biasing mechanism, air cannot pass from opening 1310 to opening 1320. If, for example, a force is applied to connector 1350, the gate 1330 pivots about hinge 1340 and raises to an open position. As before, various biasing mechanisms can be used to hold the gate in open and closed positions.

Figure 15:
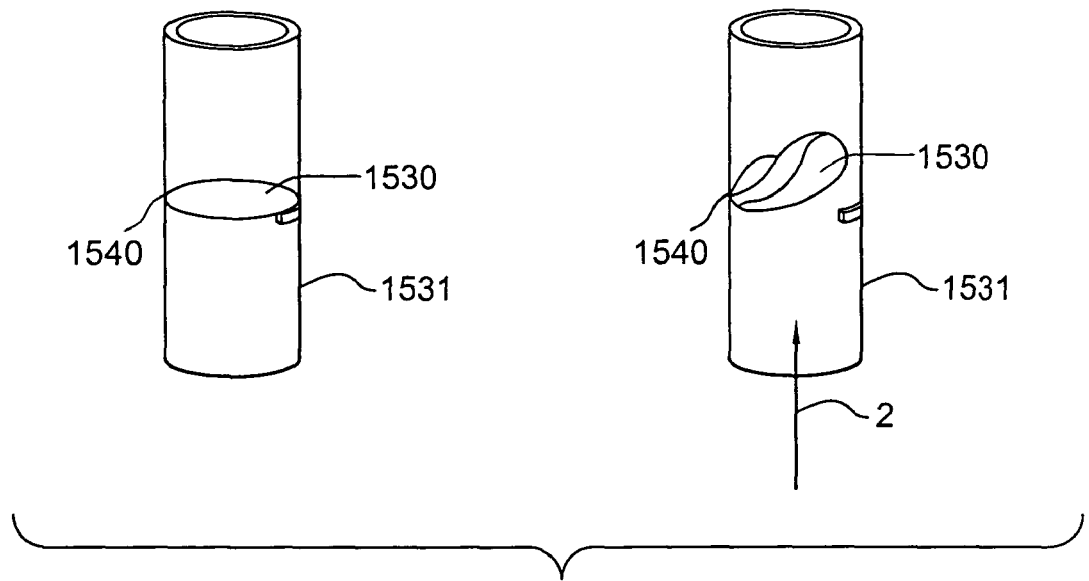
FIG. 15 shows an exemplary resilient flap backspill prevention apparatus according to an example of the present invention.

In place of a hinged-gate, a simple flap could also be used as shown in FIG. 15. The flap 1530 could be secured to the tube 1531 at a first location 1540, and be flexible enough that air 2 against a first side would cause the flap to bend and allow air to pass by. A backstop 1560 could be provided for the first side of the flap 1530 to rest against. The flap 1530 would, when the airflow ceased, resiliently return to a circular form and rest on the backstop 1560, so that water pushing against a second side opposite the first side could not cause the flap 1530 to flex in the opposite direction.

An exemplary one-way hinged-gate divider 1400 is shown in FIG. 14. In this divider, two halves 1430, 1440 of a circle of material are positioned across a passageway and connected by a hinge or a living hinge. One of the halves 1430 is fixedly attached to an inner wall of the passageway while the other half 1440 can pivot about the hinge.

According to this exemplary illustrative non-limiting implementation, the biasing mechanism that holds the hinged-gate in a closed position is a spring 1450. The spring constant on the spring is low enough that air blowing into opening 1410 can push the pivoting half of the gate 1440 to an open position. When the airflow ceases, the spring will bias the pivoting gate half 1440 to a closed position against gate-stop 1460. If an improper material, such as water, enters the passageway through opening 1420, the gate-stop 1460 will prevent the hinged-gate from swinging in the other direction.

Figure 16:
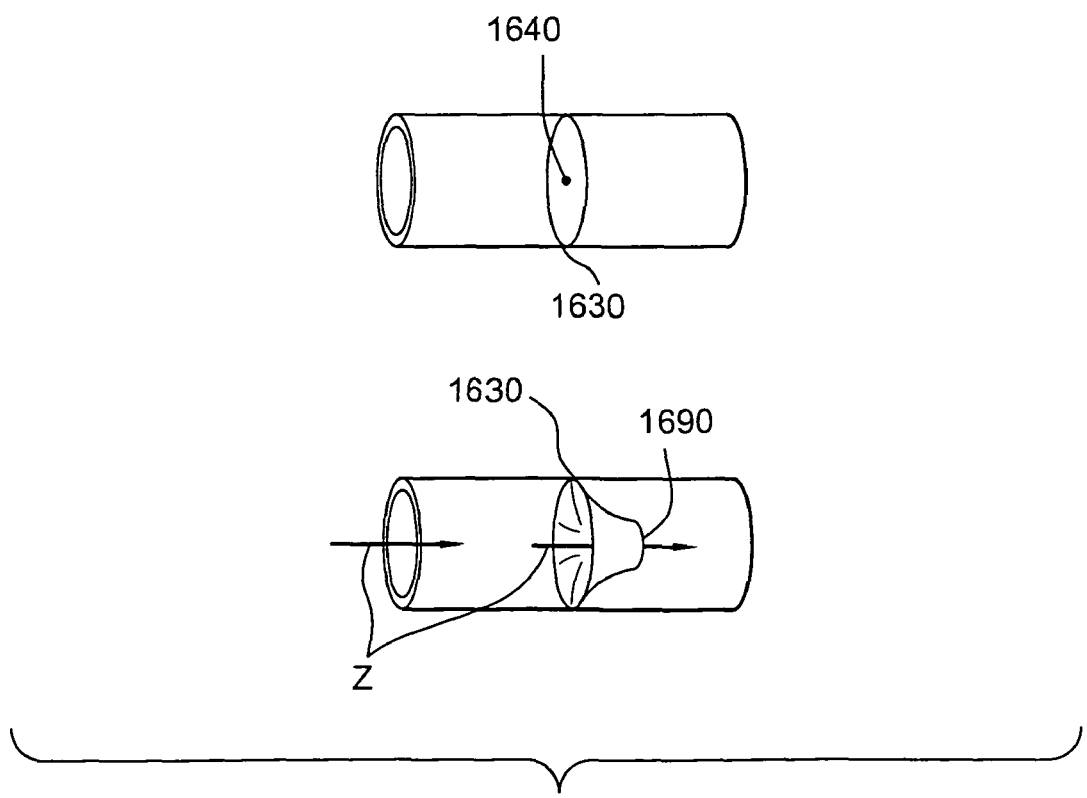
FIG. 16 shows an exemplary valve diaphragm backspill prevention apparatus according to an example of the present invention.

Still another possible exemplary divider implementation is shown in FIG. 16. This implementation includes a flexible diaphragm 1630 having a small hole 1640 in the center thereof. Air 2 pressure can cause the hole 1640 to expand and allow the air 2 to pass therethrough. When there is insufficient pressure, however, the hole 1640 contracts and blocks the passageway. Although this particular implementation may not be able to prevent all water passage, it should still provide protection against at least partial water passage towards the motor.

Although a variety of possible exemplary divider implementations have been presented herein, they are presented for illustrative purposes only and not intended to limit the scope of the invention in any way. Numerous different dividers can be used to achieve the blocking and unblocking of the passageway. Also, although blocking the passageway is generally discussed as being the divider location when the machine is turned off and unblocking the passageway is generally discussed as being the divider location when the machine is turned on, the blocking can also be designed to take place under other circumstances. For example, the blocking may occur in the presence of water in the vicinity of the divider.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. Furthermore, each individual component of any given assembly, one or more portions of an individual component of any given assembly, and various combinations of components from one or more embodiments may include one or more ornamental design features. In addition, while the invention has particular application to patients who suffer from OSA, it is to be appreciated that patients who suffer from other illnesses (e.g., congestive heart failure, diabetes, morbid obesity, stroke, barriatric surgery, etc.) can derive benefit from the above teachings. Moreover, the above teachings have applicability with patients and non-patients alike in non-medical applications.

What is claimed is:

1. A solenoid backspill prevention apparatus comprising:
a receiving chamber including an at least a partially closed end and at least one first hollow interior portion;
a first magnet having a hollow center, provided to said at least one hollow interior portion,
an engaging solenoid having a distance from a center thereof to an outer edge thereof smaller than a distance from a center of said hollow center to an outer edge thereof and interfacing with said hollow center of said first magnet such that at least a portion of said engaging solenoid is provided to said hollow center of said first magnet, said engaging solenoid including at least a first backspill stop provided to an end thereof; and
said backspill stop including at least one piece of magnetically attractable material, capable of being attracted by a magnetic force;
a housing, provided with a plurality of openings, at least partially enclosing said receiving chamber, first magnet, engaging solenoid and piece of material, and including at least one piece of magnetic material provided thereto, wherein a magnetic field generated by said magnetic material is capable of attracting said magnetically attractable material, and wherein at least one of said openings is smaller across than said backspill stop and is arranged in substantial axial alignment with said backspill stop.

2. The apparatus of claim 1, wherein at least one of said at least one openings is surrounded by a sealing arrangement to seal against a surface of the backspill stop.

3. The apparatus of claim 1, wherein said receiving chamber further includes at least one guide hole in the partially closed end thereof; and said engaging solenoid further includes at least one guide shaft interfacing with said at least one guide hole such that at least a portion of said at least one guide shaft is seated within said at least one guide hole.

4. The apparatus of claim 3, wherein said receiving chamber further includes a linear bearing, provided to said at least one guide hole, said bearing having a hollow center, wherein a least a portion of said at least one guide shaft is seated within said hollow center of said linear bearing.

5. The apparatus of claim 1, wherein said receiving chamber includes at least an outer wall and an inner wall, wherein said first hollow interior portion is positioned between said outer and inner walls.

6. The apparatus of claim 5, wherein said engaging solenoid includes a second hollow interior portion having a greater distance across than a distance across said inner wall from a first position on an one inner wall outer side to a second position opposite said first position.

7. The apparatus of claim 1, wherein said at least one piece of attractable material includes a ring of attractable material.

8. A PAP device comprising:
 a blower operable to force air through at least one passageway; and
 the solenoid backspill prevention apparatus of claim 1, operable to seal said passageway.

* * * * *